United States Patent
Kudo et al.

(10) Patent No.: US 9,266,985 B2
(45) Date of Patent: Feb. 23, 2016

(54) SILICONE COMPOUND AND A USE THEREOF

(71) Applicant: Shin-Etsu Chemical Co., Ltd., Tokyo (JP)

(72) Inventors: Muneo Kudo, Annaka (JP); Shoji Ichinohe, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/540,709

(22) Filed: Nov. 13, 2014

(65) Prior Publication Data

US 2015/0133619 A1     May 14, 2015

(30) Foreign Application Priority Data

Nov. 14, 2013    (JP) ................................ 2013-235923
Jan. 28, 2014    (JP) .................................. 2014-13623

(51) Int. Cl.

| | | |
|---|---|---|
| G02B 1/04 | (2006.01) |
| C08F 30/08 | (2006.01) |
| C08G 77/26 | (2006.01) |
| C08F 130/08 | (2006.01) |
| C07F 7/08 | (2006.01) |
| C08G 77/04 | (2006.01) |
| C08G 77/38 | (2006.01) |
| C07F 7/18 | (2006.01) |
| B65B 55/02 | (2006.01) |

(52) U.S. Cl.
CPC ............ C08F 130/08 (2013.01); C07F 7/0854 (2013.01); C07F 7/0889 (2013.01); C07F 7/1844 (2013.01); C08G 77/045 (2013.01); C08G 77/26 (2013.01); C08G 77/38 (2013.01); G02B 1/04 (2013.01); G02B 1/043 (2013.01); B65B 55/02 (2013.01)

(58) Field of Classification Search
None
See application file for complete search history.

(56) References Cited

U.S. PATENT DOCUMENTS

| 8,513,325 | B2 * | 8/2013 | Liu et al. ..................... 523/107 |
| 2007/0066706 | A1 * | 3/2007 | Manesis et al. ............... 523/106 |
| 2008/0182956 | A1 * | 7/2008 | Stanbro et al. ............... 526/260 |
| 2009/0276042 | A1 * | 11/2009 | Hughes et al. ............... 623/6.56 |
| 2009/0299022 | A1 * | 12/2009 | Ichinohe ...................... 526/279 |
| 2012/0283381 | A1 | 11/2012 | Tamiya et al. |
| 2013/0172592 | A1 * | 7/2013 | Li et al. ........................ 556/419 |

FOREIGN PATENT DOCUMENTS

| JP | 59-78236 A | 7/1984 |
| JP | 2001-55446 A | 2/2001 |
| JP | 2007-1918 A | 1/2007 |
| JP | 2007-186709 A | 7/2007 |
| JP | 2008-019402 A | 1/2008 |
| JP | 4646152 B2 | 3/2011 |
| JP | 4882136 B2 | 2/2012 |
| JP | 2012-236887 A | 12/2012 |
| JP | 2013-112776 | * 6/2013 |
| JP | 2013-112776 A | 6/2013 |
| JP | 2013-222141 | * 10/2013 |
| WO | WO 2006/026474 A1 | 3/2006 |
| WO | WO 2012/118685 A2 | 9/2012 |
| WO | WO 2013/191861 | * 12/2013 |

OTHER PUBLICATIONS

Product data sheet for Gelest MCR-C12.*
EP Seach Report dated Sep. 17, 2015 for EP Application No. 15163393.0.

* cited by examiner

Primary Examiner — Marc Zimmer
(74) Attorney, Agent, or Firm — Birch, Stewart, Kolasch & Birch, LLP

(57) ABSTRACT

One of the purposes of the present invention is to provide a silicone compound which has a specific number of silicon atoms, is well compatible with (meth)acryl monomers, is suitable as an ophthalmic monomer and provides a polymer having excellent durability of mechanical strength in a buffered phosphate solution. Another purpose of the present invention is to provide a silicone compound which functions well as a crosslinking agent for a polymerizable monomer. Further, another purpose is to provide a method for preparing the silicone compound, in particular the silicone compound having one specific structure at a high ratio. In the first aspect, the present invention provides a compound represented by the following formula (1-1):

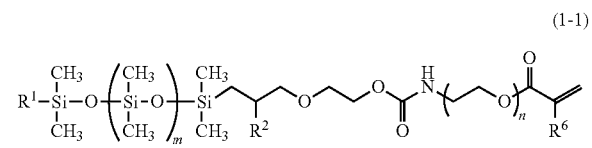

(1-1)

and a method for preparing the silicone compound. In the second aspect, the present invention provides a compound represented by the following formula (2-1):

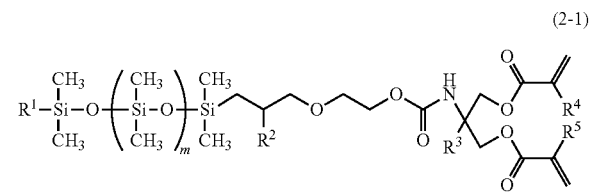

(2-1)

and a method for preparing the silicone compound.

13 Claims, 1 Drawing Sheet

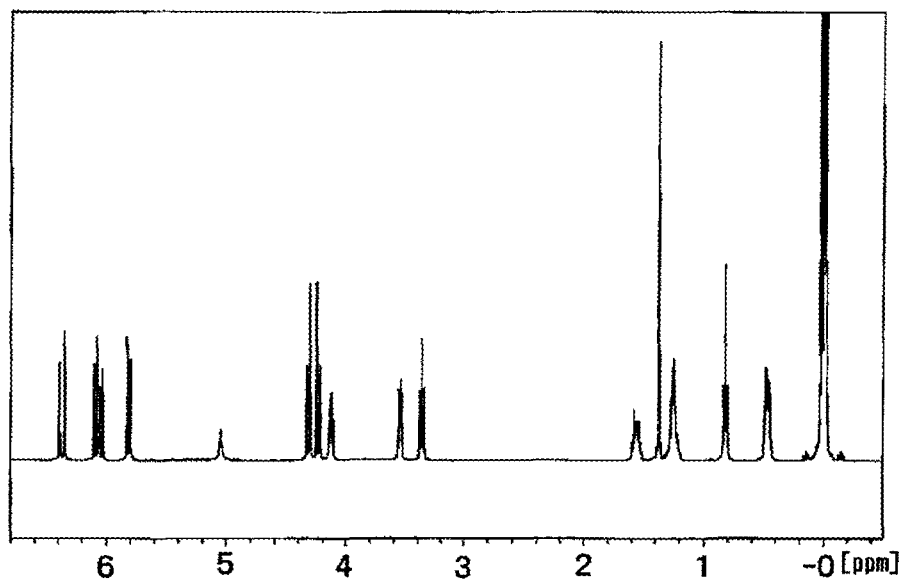

SILICONE COMPOUND AND A USE THEREOF

CROSS REFERENCE

This application claims the benefits of Japanese Patent Application Nos. 2013-235923 filed on Nov. 14, 2013, and 2014-013623 filed on Jan. 28, 2014, the contents of which are hereby incorporated by reference.

FIELD OF THE INVENTION

The present invention relates to a silicone compound which is useful as starting materials for preparing ophthalmic devices such as contact lenses, intraocular lenses and artificial corneas, hereinafter also referred to as ophthalmic monomer, and a method for the preparation thereof. Specifically, the present invention relates to a silicone compound which has a silicone moiety having a specific weight and is copolymerizable with the other polymerizable monomer such as a (meth) acryl monomer to provide a polymer having high transparency and oxygen permeability and being suitable for ophthalmic uses, and a method for preparing the silicone compound.

Further, the present invention relates to a silicone compound which has a silicone moiety having a specific weight and a (meth)acryl group, is copolymerizable with the other polymerizable monomer to provide a polymer having high transparency and oxygen permeability and being suitable for ophthalmic uses, and in particular, functions as a crosslinking component for a polymerizable silicone monomer, and a method for preparing the silicone compound.

The following silicone compounds are known as an ophthalmic monomer.

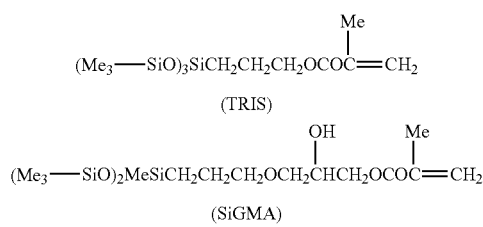

The afore-mentioned TRIS, 3-[tris(trimethylsiloxy)silyl] propyl methacrylate, has poor compatibility with hydrophilic monomers such as 2-hydroxyethyl methacrylate (HEMA). Therefore, when TRIS is copolymerized with a hydrophilic monomer, there is such a disadvantage that a transparent polymer is not obtained. In contrast, SIGMA described above has good compatibility with hydrophilic monomers such as HEMA. The copolymers obtained from SIGMA have relatively high oxygen permeability and high hydrophilicity. Recently, higher oxygen permeability is required for an ophthalmic polymer so as to be used continuously on eyes for a longer term. Polymers obtained from SiGMA do not have sufficient oxygen permeability.

In order to solve this problem, Japanese Patent Application Laid-Open No. 2007-186709, Patent Literature 1, describes a compound represented by the following formula (a).

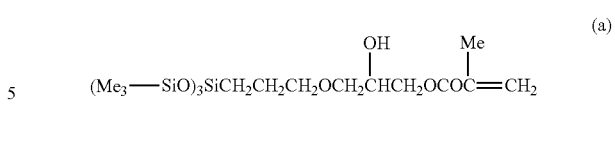

In the afore-mentioned SIGMA, the weight ratio of the Si-containing moiety, i.e. bis(trimethylsiloxy)methylsilyl, to the whole molecule is 52%. In contrast, in the aforesaid formula (a), the weight ratio of the Si-containing moiety, i.e. tris (trimethylsiloxy)silyl, to the whole molecule is 60%. The compound represented by the formula (a) thus has the higher weight ratio of the Si-containing moiety and, therefore, gives higher oxygen permeability to ophthalmic devices.

However, there is a problem such that when the weight ratio of the Si-containing moiety is increased in order to improve oxygen permeability, the mole weight of the polymerizable group became large and, therefore, strength of the copolymer decreased. Japanese Patent Application Laid-Open No. 2007-1918, Patent Literature 2, describes that the compound represented by the aforesaid formula (a) is prepared by a reaction of a corresponding epoxy precursor and methacrylic acid. There is such a problem such that many side reactions occur and the physical properties of the resulting copolymers vary.

As described in the column of the technical background in Japanese Patent No. 4646152, Patent Literature 5, it is known that a silicone having a tetrameric or more structure is thought to be preferable in term of oxygen permeability and, in particular, a silicone having a tetrameric or pentameric structure is thought to be more preferable in order to balance between oxygen permeability and strength of the copolymer. Therefore, development of a method for preparing a silicone monomer having a tetrameric or more structure with a high purity is desired.

Japanese Patent Application Laid-Open No. Sho 59-78236, Patent Literature 3, describes a method for the preparation of a silicone compound represented by a following formula (b), comprising steps of anion-polymerizing a cyclic siloxane in the presence of a lithium trialkylsilanolate as an initiator and, then, reacting the reaction product with a chlorosilane having a (meth)acryl group, such as 3-(2-methacryloyloxy ethoxy) propyl dimethyl chlorosilane.

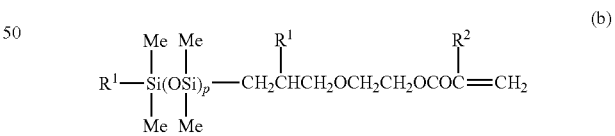

However, when the silicone compound obtained in the aforementioned method is mixed with a hydrophilic monomer, such as 2-hydroxyethyl methacrylate, turbidity occurs sometimes. Further, a ratio of terminals of the silicone chain blocked with the chlorosilane is not high.

Japanese Patent Application Laid-Open No. 2001-55446, Patent Literature 4, describes a method for preparing a silicone compound represented by the following formula (c) by esterifying (meth)acrylic acid or transesterifying (meth)acrylate with an organopolysiloxane having a hydroxyl group at the one terminal,

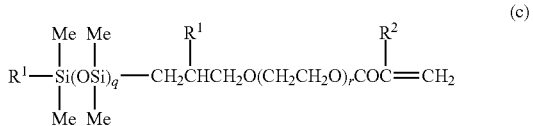

wherein r is an integer of 3 or larger.
However, the esterification ratio is insufficient, the blocked terminal ratio is low, and the compound has broad distribution of a polymerization degree of the silicone moiety.

Japanese Patent No. 4646152, Patent Literature 5, describes a method for preparing a high purity silicone monomer represented by the following formula (d) by esterifying an organopolysiloxane having a hydroxyl group at the one terminal and a (meth)acrylic acid halide:

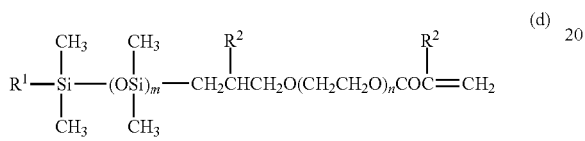

wherein m is one value out of the integers of from 3 to 10, n is one value out of 1 and 2, $R^1$ is only one out of alkyl groups having 1 to 4 carbon atoms, and $R^2$ is only one out of a hydrogen atom and a methyl group,
and more than 95 weight % of the compound is one kind of compound having the specific one structure, i.e., each one value of m, n, $R^1$ and $R^2$.

Japanese Patent No. 9882136, Patent Literature 6, describes a compound represented by the following formula (M1) and an ophthalmic lens prepared from a polymer having repeating units derived from the compound.

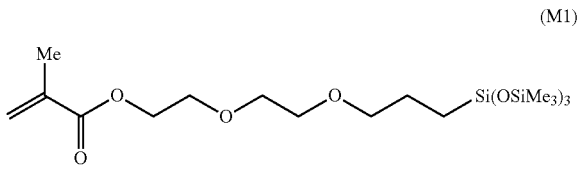

Japanese Patent Application Laid-Open No. 2013-112776, Patent Literature 7, describes a (meth)acryl group containing organopolysiloxane represented by the following formula (I).

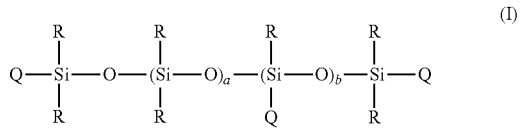

wherein R is an unsubstituted or substituted monovalent hydrocarbon or alkoxy group which has 1 to 20 carbon atoms and no (meth)acryl group. Q is, independently of each other, represented by the following "A" or "X", provided that at least one Q is "A". A is a group represented by —$R^1$—CONH—C($R^2$) [CH$_2$—O—CO—CH=CH$_2$]$_2$ or —$R^1$—CONH—C($R^2$) [CH$_2$—O—CO—C(CH$_3$)=CH$_2$]$_2$, wherein $R^1$ is a divalent organic group, $R^2$ is a an unsubstituted or substituted monovalent hydrocarbon group, which has 1 to 20 carbon atoms or an alkoxy group and no (meth)acryl group. X is selected from the groups defined for R and a monovalent organic group which has an active hydrogen atom and no (meth)acryl group. "a" is an integer of from 0 to 1,000 and "b" is and integer of from 0 to 100.

PRIOR LITERATURES

Patent Literature 1: Japanese Patent Application Laid-Open No. 2007-186709
Patent Literature 2: Japanese Patent Application Laid-Open No. 2007-1918
Patent Literature 3: Japanese Patent Application Laid-Open No. Sho 59-78236
Patent Literature 4: Japanese Patent Application Laid-Open No. 2001-55446
Patent Literature 5: Japanese Patent No. 4646152
Patent Literature 6: Japanese Patent No. 4882136
Patent Literature 7: Japanese Patent Application Laid-Open No. 2013-112776

SUMMARY OF THE INVENTION

However, the monomeric compound described in Patent Literature 5, sometimes has poor compatibility with other (meth)acryl monomers to be used together, in particular fluorinated substituent group-containing (meth)acryl monomers which provide stain resistance. Further, a polymer obtained from the monomeric compound may have insufficient durability of mechanical strength in a buffered phosphate solution.

The monomeric compound described in Patent Literature 6 sometimes has poor compatibility with other (meth)acryl monomers to be used together, in particular fluorinated substituent group-containing (meth)acryl monomer which provides stain resistance.

Patent Literature 6, claim 3, also describes a monomer having a urethane bond. However, this monomer has such a siloxane structure as tris(trimethylsiloxy) silyl, bis(trimethylsiloxy)methylsilyl and pentamethyldisiloxane, and does not has a chain siloxane structure. A polymer obtained from a monomer of this structure may have lower oxygen permeability or a bad shape recovery property.

Therefore, one of the purposes of the first aspect of the present invention is to provide a silicone compound which has a specific number of silicon atoms, is well compatible with (meth)acryl monomers, in particular fluorinated substituent group-containing (meth)acryl monomers, is suitable as an ophthalmic monomer and provides a polymer having excellent durability of mechanical strength in a buffered phosphate solution. Another purpose is to provide a method for preparing the silicone compound, in particular a silicone mixture which contains, at a high ratio, a silicone compound having one specific structure.

Further, an additional polymerizable monomer is often used as a crosslinking agent to increase a crosslinking degree of a polymer having repeating units derived from an ophthalmic silicone monomer so as to increase durability of mechanical strength in a buffered phosphate solution. For instance, polyfunctional (meth)acrylates such as ethylene glycol dimethacrylate are used as the crosslinking agent. However, the polyfunctional (meth)acrylate does not have a silicone chain and, therefore, oxygen permeability of a polymer obtained is lower sometimes or a crosslinking degree of a polymer is sometimes too high, so that shrinkage may cause in curing and dimension stability may be bad.

Therefore, a silicone compound is desired which well works as a crosslinking agent for a polymerizable silicone monomer and provides a polymer having higher oxygen permeability, excellent durability of mechanical strength in a buffered phosphate solution and dimension stability. The silicone compound described in Patent Literature 5 have only one (meth)acryl group and does not work as a crosslinking agent. Further, a polymer obtained from the compound has poor a durability of mechanical strength in a buffered phosphate solution. The silicone compounds described in Patent Literature 6 also have only one (meth)acryl group and does not work as a crosslinking agent. Further, the silicone compound described in Patent Literature 6 has an ethylene oxide-ethylene oxide structure between a siloxane structure and a (meth)acryl structure. This structure may have too high hydrophilicity and has poor compatibility with other (meth) acryl monomers, in particular fluorinated substituent group-containing (meth)acryl monomers.

The silicone compound described in Patent Literature 7 has plural (meth)acryl groups in the molecular, so that has high cross-linking efficiency. However, the silicone compound has poor compatibility with other polymerizable monomers. Further, the silicone compound has many siloxane units. The silicone compound is prepared by reacting an organopolysiloxane modified with a monovalent organic group having an active hydrogen atom and an isocyanate compound having a hydrocarbon group with two (meth)acryl groups. The organopolysiloxane has many siloxane units and large molecular weight distribution and, therefore, the purity of the organopolysiloxane is low and a polymer obtained is a mixture of polymers. Further, a polymer obtained from the Monomer has poorer transparency. The monomer having a silicone chain which has a higher polymerization degree has sometimes poor compatibility with other polymerizable monomers to cause turbidity.

Therefore, one of the purposes of the second aspect of the present invention is to provide a silicone compound which functions well as a crosslinking agent for a polymerizable monomer. Specifically, the purpose is to provide a silicone compound which is well compatible with polymerizable silicone monomers and other polymerizable monomers to provide a polymer having high oxygen permeability, excellent durability of mechanical strength in a buffered phosphate solution and excellent dimension stability. The other purpose is to provide a silicone mixture which contains, at a high ratio, a silicone compound having one specific structure and a method for preparing the silicone compound.

The present inventors have made research to solve the afore-mentioned problems of the first aspect and found that a compound represented by the following formula (1-1) is well compatible with other (meth)acryl monomers and provides a colorless and transparent polymer which has excellent durability of mechanical strength in a buffered phosphate solution.

Thus, in the first aspect, the present invention provides a compound represented by the following formula (1-1):

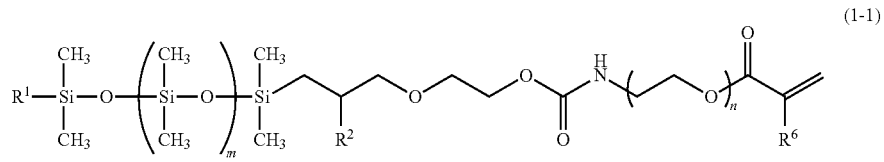

(1-1)

wherein m is an integer of from 2 to 10, n is 1 or 2, $R^1$ is an alkyl group having 1 to 4 carbon atoms, and $R^2$ and $R^6$ are, independently of each other, a hydrogen atom or a methyl group, and a method for preparing the silicone compound represented by the formula (1-1).

Further, the present inventors have made research to solve the afore-mentioned problems of the second aspect and found that a compound represented by the following formula (2-1) is well compatible with other polymerizable silicone monomers and other polymerizable monomers and provides a colorless and transparent polymer.

Thus, in the second aspect, the present invention provides a compound represented by the following formula (2-1):

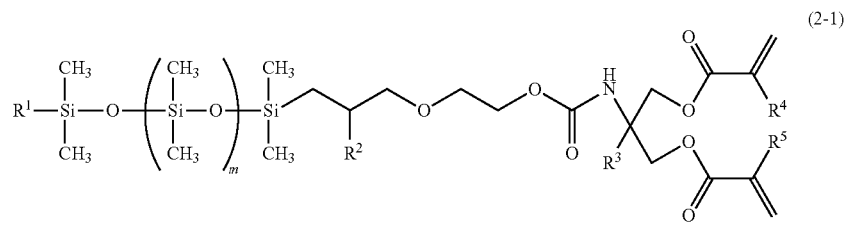

(2-1)

wherein m is an integer of from 2 to 10, $R^1$ is an alkyl group having 1 to 4 carbon atoms, $R^2$ is a hydrogen atom or a methyl group, $R^3$ is a substituted or unsubstituted monovalent hydrocarbon group which has no (meth)acryl group and has 1 to 20 carbon atoms, or an alkoxy group having 1 to 10 carbon atoms, $R^4$ is a hydrogen atom or a methyl group, and $R^5$ is a hydrogen atom or a methyl group, and a method for preparing the silicone compound represented by the formula (2-1).

The compound represented by the aforesaid formula (1-1) in the first aspect is well compatible with other polymerizable monomers, such as (meth)acryl monomers, to thereby provide a colorless and transparent polymer by copolymerization. In particular, the compound has excellent compatibility with fluorinated substituent group-containing (meth)acryl monomers which provides stain resistance to provide a polymer having good hydrophilicity and stain resistance. Additionally, the compound comprises the specific amount of silicone atoms, so that a polymer obtained has higher oxygen permeability. Further, the compound has a urethane bond in a spacer structure in the molecular and, therefore, a polymer obtained forms hydrogen bonds between polymers and has excellent durability of mechanical strength in a buffered phosphate solution. Further, the present method provides a compound having one kind of specific structure at a high ratio. Accordingly, the present compound and the present method are useful for preparing ophthalmic devices.

The compound represented by the aforesaid formula (2-1) in the second aspect of the present invention is well compatible with other polymerizable monomers, in particular, polymerizable silicone monomers and functions well as a crosslinking component. Further, the silicone compound has one specific structure at a high ratio. Therefore, the silicone compound copolymerizes with another polymerizable monomer to provide a colorless and transparent polymer having excellent durability of mechanical strength in a buffered phosphate solution. In particular, the silicone compound is well compatible with fluorinated substituent group-containing (meth)acryl monomers which provides stain resistance to provide a polymer having good hydrophilicity and stain resistance. Additionally, a polymer obtained from the silicone compound has higher oxygen permeability. Further, the present method provides a silicone compound having a high blocked terminal ratio and a high ratio of one specific structure. Accordingly, the present compound and the present method are useful for preparing ophthalmic devices.

BRIEF EXPLANATION OF THE DRAWING

FIG. 1 is a chart of $^1$H-NMR spectra of the silicone compound prepared in Example 2-1.

DETAILED DESCRIPTION OF THE INVENTION

[Compound in the First Aspect]

The compound represented by the aforesaid formula (1-1) has a urethane bond in the spacer part which bonds a (meth) acryl structure and a siloxane structure. Therefore, the urethane bonds form hydrogen bonds between polymers to provide a polymer having excellent durability of mechanical strength. In the formula (1-1), n is 1 or 2. That is, the compound is also characterized in that a part bonding the urethane structure and the siloxane structure has one-ethylene oxide structure, and a part binding the urethane structure and the (meth)acryl structure has one- or two-ethylene oxide structure.

If the part bonding the urethane structure and the siloxane structure has two- or more-ethylene oxide structure, hydrophilicity of the compound is too high, so that its compatibility with (meth)acryl monomers, in particular, fluorinated substituent group-containing (meth)acryl monomers, is poor. If the part has propylene oxide structure instead of the ethylene oxide structure, the compound has good compatibility with the fluorinated substituent group-containing (meth)acryl monomers, but hydrophobicity of a polymer obtained is too high and poor hydrophilicity. Further, if the part has a polyalkylene oxide structure, mechanical strength of a polymer obtained is weak. It is preferred that hydrophilicity of the part bonding the urethane structure and the siloxane structure is not so high in order to make a good balance of the properties.

If the part bonding the urethane structure and the (meth) acryl structure has no ethylene oxide structure, the compound has insufficient hydrophilicity. If the part has three- or more-ethylene oxide structure, its hydrophilicity is too high and, therefore, after washing with water, a high ratio of one specific structure is not attained. Further, the raw material (meth) acryl group containing isocyanate are not easy available. Further, its compatibility with (meth)acryl monomers, in particular fluorinated substituent group-containing (meth) acryl monomers, is worse.

In the aforesaid formula (1-1), m is an integer of from 2 to 10, preferably 3 to 7, more preferably 3. If m is smaller than the lower limit, oxygen permeability of a polymer is worse. If m is larger than the upper limit, hydrophilicity of a polymer is worse. When m is within the aforesaid limits, the compound has a linear siloxane structure having the desired amount of silicon atoms, so that a polymer obtained has good oxygen permeability and shape recovery property.

In the aforesaid formula (1-1), $R^1$ is an alkyl group having 1 to 4 carbon atoms, preferably a butyl group. $R^2$ and $R^6$ are, independently of each other, a hydrogen atom or a methyl group.

The present method of the invention provides one kind of compound which is represented by the formula (1-1) and has one specific structure at a high ratio, as will described below. One kind of compound having one specific structure means that a compound has a specific one value of m, n, $R^1$, $R^2$ and $R^6$. A high ratio means that an amount of the aforesaid one kind of compound, based on a total amounts of the compound represented by the formula (1-1), is more than 95 mass %, preferably 99 mass % or more. In the present invention, the ratio is determined in gas chromatography, hereinafter referred to as "GC". The details of GC will be described below. When the compound is mixed with a non-silicone monomer such as 2-hydroxyethyl methacrylate, any turbidity does not occur and a transparent polymer is obtained, because the starting compound has a high ratio of one specific structure.

In particular, preferred is a compound in which m is 3, and further preferred is a compound in which m is 3 and $R^1$ is a butyl group. When $R^1$ is a butyl group, $R^2$ and $R^6$ are a hydrogen atom, m is 3 and n is 2 in the formula (1-1), the molecular weight of the compound is 713 and a content of the dimethylpolysiloxane chain moiety is approximately 50 mass %, based on the total mass of the compound. That is, the compound comprises a large amount of Si atoms, whereby a polymer obtained has high oxygen permeability.

[Compound of the Second Aspect]

The present component of the second aspect is represented by the aforesaid formula (2-1) and characterized in that the compound has one-ethylene oxide structure and a urethane bond in the spacer part which bonds a (meth)acryl structure and a siloxane structure and has two (meth)acryl groups at the one terminal. On account of these characters, the compound is well compatible with other silicone monomers having a polymerizable group and other polymerizable monomers. Further, the urethane bonds form hydrogen bonds between polymers to provide a polymer having excellent durability of mechanical strength. Additionally, on account of the two (meth)acryl groups, the compound functions well as a crosslinking component to provide a polymer having excellent durability of mechanical strength and dimension stability.

The silicone compound of the second aspect has only one ethylene oxide in the spacer part which bonds a (meth)acryl structure and a siloxane structure and, therefore, the compound has proper hydrophilicity. If the silicone compound has no ethylene oxide structure, hydrophilicity of the compound is insufficient. If the part has two- or more-ethylene oxide structure, hydrophilicity of the compound is too high, so that its compatibility with (meth)acryl monomers, in particular fluorinated substituent group-containing (meth)acryl monomers, is poor. If the part has a propylene oxide instead of the ethylene oxide, the compound has good compatibility with fluorinated substituent group-containing (meth)acryl monomers, but hydrophobicity of a polymer obtained is too high and hydrophilicity is insufficient. Further, if the part has a polyalkylene oxide structure, mechanical strength of a polymer obtained is worse.

In the aforesaid formula (2-1), m is an integer of from 2 to 10, preferably 3 to 7, more preferably 3. When m is within the aforesaid limits, the compound has a linear siloxane structure having a desired amount of silicon atoms, so that a polymer obtained has high oxygen permeability and good shape recovery property. If m is smaller than the lower limit, oxygen permeability of a polymer is worse. If m is larger than the upper limit, hydrophilicity of a polymer is worse. Further, if m is larger than the upper limit, a starting siloxane for the compound has wide distribution of the molecular weight and a ratio of one specific structure in a silicone compound obtained tends to be lower.

In the aforesaid formula (2-1), $R^1$ is an alkyl group having 1 to 4 carbon atoms, preferably a butyl group. $R^2$ is a hydrogen atom or a methyl group. $R^3$ is a substituted or unsubstituted monovalent hydrocarbon group which has no (meth)acryl group and has 1 to 20, preferably 1 to 10 carbon atoms, or an alkoxy group having 1 to 10, preferably 1 to 6 carbon atoms. Examples of the monovalent hydrocarbon group include alkyl groups such as a methyl group, an ethyl group, a propyl group, a butyl group, a pentyl group, a hexyl group, a heptyl group, an octyl group, a nonyl group and a decyl group; cycloalkyl groups such as a cyclopentyl group and a cyclohexyl group; aryl groups such as a phenyl group and a tolyl group; alkenyl groups such as a vinyl group and an allyl group; and those hydrocarbon groups wherein a part or all of the hydrogen atoms bonded to the carbon atoms of these groups are substituted with a halogen atom such as a chlorine atom and a fluorine atom. Among these, a methyl group, an ethyl group, a propyl group and a butyl group are preferable and a methyl group is particularly preferable. $R^4$ is a hydrogen atom or a methyl group, and $R^5$ is a hydrogen atom or a methyl group.

The present method of the invention provides one kind of compound which is represented by the formula (2-1) and has one specific structure at a high ratio, as will described below. One kind of compound having one specific structure means a compound having a specific one value of m, $R^1$, $R^2$, $R^3$, $R^4$ and $R^5$. A high ratio means that an amount of the aforesaid one kind of compound, based on a total amounts of the compound represented by the formula (2-1), is more than 95 mass %, preferably 99 mass % or more. In the present invention, the ratio is determined in gas chromatography, hereinafter referred to as "GC". The details of GC will be described below. When the compound is mixed with a non-silicone monomer such as 2-hydroxyethyl methacrylate, any turbidity does not occur and a transparent polymer is obtained, because the starting compound has a high ratio of one specific structure.

In particular, preferred is a compound in which m is 3, and further preferred is a compound in which m is 3 and $R^1$ is a butyl group. When $R^1$ is a butyl group, $R^2$, $R^4$ and $R^5$ are a hydrogen atom, $R^3$ is a methyl group and m is 3 in the formula (2-1), the molecular weight is 753 and a content of the dimethylpolysiloxane chain moiety is approximately 47 mass %, based on the total mass of the compound. That is, the compound comprises a large amount of Si atoms whereby a polymer obtained has high oxygen permeability.

Method for the Preparation

The present invention further provides methods for preparing the afore-mentioned compound represented by the formula (1-1) or (2-1).

A method for preparing the compound represented by the formula (1-1) comprises a step of reacting a silicone compound represented by the following formula (3):

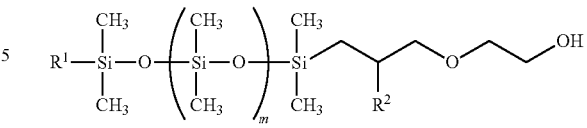

(3)

wherein m, $R^1$ and $R^2$ are as defined above;
with a (meth)acryl group-containing isocyanate compound represented by the following formula (4):

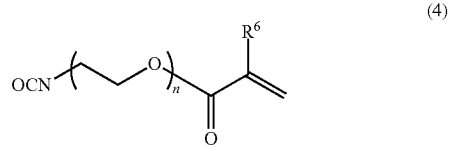

(4)

wherein n and $R^6$ are as defined above.

The reaction is preferably carried out in such a manner that the aforesaid compound (4) is slowly added to the aforesaid compound (3) with no solvent or to a solution of the aforesaid compound (3) in toluene or hexane, and reacted at a temperature of from 0 to 50 degrees C. with being cooled, for instance, in a water bath.

The amount of the compound (4) is 1 to 3 moles, preferably 1.05 to 2 moles, per mole of the component (3). If the amount is smaller than the lower limit, the unreacted compound (3) would remain in the reaction product and a high ratio of one specific structure is not attained. If the amount is larger than the upper limit, this is economically disadvantageous.

A method for preparing the compound represented by the formula (2-1) comprises a step of reacting a silicone compound represented by the following formula (3):

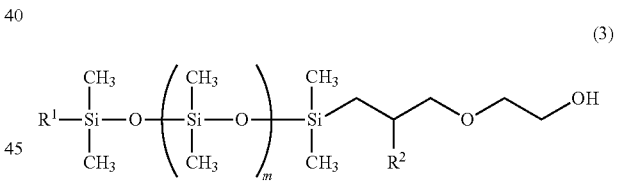

(3)

wherein m, R' and $R^2$ are as defined above;
with a (meth)acryl group-containing isocyanate compound represented by the following formula (5):

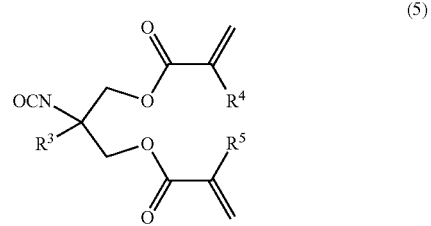

(5)

wherein $R^3$, $R^4$ and $R^5$ are as defined above.

The reaction is preferably carried out in such a manner that the aforesaid compound (4) is slowly added to the aforesaid compound (3) with no solvent or to a solution of the aforesaid compound (3) in toluene or hexane, and reacted at a temperature of from 0 to 50 degrees C. with being cooled, for instance, in a water bath.

The amount of the compound (5) is 1 to 3 moles, preferably 1.05 to 2 moles, per mole of the component (3). If the amount is smaller than the lower limit, the unreacted compound (3) would remain in the reaction product and a high ratio of one specific structure is not attained. If the amount is larger than the upper limit, this is economically disadvantageous.

The afore-mentioned reactions may be carried in the presence of a catalyst. Any catalyst generally used for isocyanate reactions may be used. Preferred are tin compound catalysts and amine catalysts. As the tin compound catalysts, a tin (II) salt of carboxylic acid is preferred for its catalyst activity. As the amine catalysts, tertiary amines, such as triethylamine, tributylamine and N-ethyldiisopropylamine are preferred. The amount of the catalyst may be 0.001 to 0.1 part by mass, preferably 0.005 to 0.05 part by mass, per 100 parts by mass of the component (3). If the amount is larger than the upper limit, the catalyst effect may saturate and this is not economically. If the amount is smaller than the lower limit, an enough catalyst effect is not attained, so that the reacting rate is slow and productivity is worse.

It is preferred that the unreacted silicone compound (3) is monitored in GC. After disappearance of its peak is confirmed, an alcohol, such as methanol or ethanol, is poured into the reaction mixture to inactivate the isocyanate group of the unreacted isocyanate compound. Subsequently, an organic solvent and water are added to the mixture and stirred and, then, left standing to allow separation into an organic phase and an aqueous phase. The organic phase is washed several times with water and, then, a silicone compound (1-1) or (2-1) which has one specific structure is obtained at a high ratio by stripping off the solvent present in the organic phase because almost no side reaction occurs.

The silicone compound (3) may be prepared by addition reacting a polyorganohydrogen siloxane represented by the following formula (6):

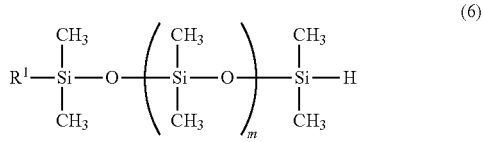
(6)

wherein m and R' are as defined above,
with ethylene glycol mono(meth)allyl ether represented by the following formula (7):

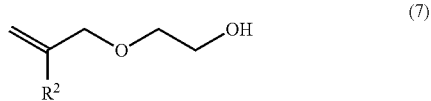
(7)

wherein $R^2$ is as defined above.

This addition reaction may be carried out in any conventional manners. For instance, the reaction is carried out in the presence of a hydrosilylation catalyst. A solvent may be used. Examples of the solvent include aliphatic or aromatic solvents such as hexane and toluene; and alcoholic solvents such as ethanol and IPA. The amount of the allyl ether compound is 1.2 moles or more, preferably 1.5 moles or more, per mole of the polyorganohydrogen siloxane.

Examples of the ethylene glycol mono(meth)allyl ether include ethylene glycol monoallyl ether and ethylene glycol monomethallyl ether.

It is preferred that the ally ether compound is optionally diluted with a solvent to which, then, a hydrosilylation catalyst of platinum family is added. Any conventional hydrosilylation catalysts of platinum family may be used and not limited to any particular one. Subsequently, the polyorganohydrogen siloxane is added dropwise to the mixture to react at room temperature or a higher temperature. After the completion of the addition, the reaction mixture is held under heating, until disappearance of the peak of the raw material, polyorganohydrogen siloxane, is confirmed, for instance, in GC. After the end point of the reaction is confirmed in GC, the unreacted polyorganohydrogen siloxane does not remain in a product, so that a silicone compound obtained has one specific structure at a higher ratio. The aforesaid addition reaction may be conducted in one step.

After the completion of the addition reaction, an excessive allyl ether compound is removed from the reaction liquid. For instance, the reaction liquid is subjected to stripping under a reduced pressure, or washed with ion exchanged water or an aqueous sodium sulfate solution to extract the allyl ether compound into an aqueous phase. Here, a proper amount of solvent, such as toluene and hexane, may preferably be used to attain clear phase separation. In particular, the solvent is stripped off from the organic phase under a reduced pressure, whereby the silicone compound represented by the aforesaid formula (3) and having a high ratio of one specific structure such as more than 95 mass %, even approximately 97 mass % or more, is obtained. The silicone compound may be distilled twice or more to further increase the ratio.

The polyorganohydrogen siloxane represented by the aforesaid formula (6) may be prepared in known manners. For instance, the compound (6) wherein $R^1$ is a butyl group and m is 3, i.e. monobutyl decamethyl hydropentasiloxane, may be prepared by the steps of first synthesizing $BuMe_2SiOLi$ using BuLi, subjecting hexamethylcyclotrisiloxane to a ring-opening reaction using the $BuMe_2SiOLi$ as an initiator and, then, terminating the reaction with dimethylchlorosilane. The product is purified by distillation to obtain monobutyl decamethyl hydropentasiloxane at a ratio of 99 mass % or higher. Alternatively, the distillation may be carried out after the monobutyl decamethyl hydropentasiloxane is addition reacted with ethylene glycol mono(meth)allyl ether represented by the formula (7). However, monobutyl decamethyl hydropentasiloxane has a boiling point of 110 degrees C/2 mmHg and the product of the addition reaction has a higher boiling point. Therefore, it is preferred that the monobutyl decamethyl hydropentasiloxane is distilled before the addition reaction to increase its ratio. Then, a silicone compound (3) having one specific structure is obtained at a higher ratio.

The silicone compound (3) may be prepared also by the steps of subjecting the ethylene glycol mono(meth)allyl ether to a silylation to provide a silyl ester with a silylating agent such as hexamethyldisilazane, addition reacting the compound obtained in the aforesaid manners and, then, hydrolyzing the silyl ester.

The silicone compounds of the first and second aspects of the present invention are well compatible with other compounds having a group polymerizable with the silicone compounds, such as compounds having a (meth)acryl group, hereinafter referred to as a polymerizable monomer. Therefore, the silicone compounds copolymerize with the polymerizable monomer to provide a colorless and transparent polymer. In particular, the silicone compounds are well compatible with a fluorinated substituent group-containing (math)acryl monomer, so that good hydrophilicity and stain resistance of a polymer are obtained.

Examples of the polymerizable monomer include acryl monomers such as (meth)acrylic acid, methyl (meth)acrylate, ethyl (meth)acrylate, (poly)ethylene glycol dimethacrylate, polyalkylene glycol mono(meth)acrylate, polyalkylene glycol monoalkyl ether (meth)acrylate, trifluoroethyl (meth) acrylate, 2-hydroxyethyl (meth)acrylate, and 2,3-dihydroxypropyl (meth)acrylate; acrylic acid derivatives such as N, N-dimethyl acrylamide, N, N-diethyl acrylamide, N-acryloyl morpholine, and N-methyl (meth)acrylamide; other ethylenically unsaturated aliphatic or aromatic compound such as crotonic acid, cinnamic acid, and vinyl benzoic acid; and polymerizable group-containing silicone compounds. These may be used singly or two or more of them may be used in combination.

Additionally, the silicone compound in the present second aspect has two (meth)acryl groups, so that it functions well as a crosslinking component. Therefore, the silicone compound is useful as a crosslinking agent for a polymerizable monomer and provides a colorless and transparent polymer having good durability of mechanical strength. In particular, the present compound is well compatible with a silicone monomer having a polymerizable group such as a (meth)acryl group. Any conventional polymerizable monomers known as ophthalmic monomers may be used. In particular, preferred are silicone monomers having a (meth)acryl group at the one terminal and a siloxane structure at the other terminal. For instance, silicone monomers described in Patent Literatures 1 to 6 may be used.

When the present silicone compound in the second aspect is used as a crosslinking agent, the amount of the silicone compound may preferably be 0.1 to 50 parts by mass, further preferably 0.5 to 20 parts by mass, relative to 100 parts by mass of the total amount of the other polymerizable monomers, in particular, the other polymerizable silicone monomer. Because the present silicone compound has one specific structure at a high ratio itself, a polymer obtained has high transparency.

Further, one or more other compounds which function as a crosslinking component may be polymerized with the present silicone compound and the aforesaid polymerizable monomer. The compound may be bifunctional or polyfunctional (meth)acrylates. Examples of the bifunctional acrylates include 1,4-butanediol diacrylate, 1,6-hexanediol diacrylate, neopentylglycol diacrylate, polyethylene glycol diacrylate, neopentylglycol hydroxypivalate diacrylate, dicyclopentanyl diacrylate, caprolactone-modified dicyclopentenyl diacrylate, ethylene oxide-modified phosphate diacrylate, allylated cyclohexyl diacrylate, and isocyanurate diacrylate. Examples of the polyfunctional acrylates include trimethylol propane triacrylate, dipentaerythritol triacrylate, propionic acid-modified dipentaerythritol triacrylate, pentaerythritol triacrylate, propylene oxide-modified trimethylolpropane triacrylate, tris(2-acryloxyethyl) isocyanulate, dipentaerythritol pentaacrylate, propionic acid-modified dipentaerythritol pentaacrylate, dipentaerythritol hexaacrylate, and caprolactone-modified dipentaerythritol hexaacrylate. Examples of the bifunctional methacrylates include ethylene glycol dimethacrylate, triethylene glycol dimethacrylate, 1,4-butanediol dimethacrylate, neopentylglycol dimethacrylate, 1,6-hexanediol dimethacrylate, 1,9-nonanediol dimethacrylate, 1,10-decanediol dimethacrylate, glycerin dimethacrylate, and dimethyloltricyclodecane dimethacrylate. Examples of the polyfunctional methacrylates include trimethylol propane trimethacrylate and ethoxylated trimethylol propane trimethacrylate. The amount of the compound may be preferably 0.1 to 50 parts by mass, further preferably 0.5 to 20 parts by mass, relative to 100 parts by mass of the total amount of the other polymerizable monomers.

The copolymerization of the present compound and the other polymerizable monomer mentioned just above may be carried out in conventional known manners. For instance, known polymerization initiator such as thermal polymerization initiators or photo polymerization initiators may be used. Examples of the polymerization initiator include 2-hydroxy-2-methyl-1-phenyl-propane-1-one, azobis isobutyronitrile, azobis dimethylvaleronitrile, benzoyl peroxide, tert-butyl hydroperoxide, and cumene hydroperoxide. The polymerization initiator may be used singly or two or more of them may be used in combination. The amount of the polymerization initiator is 0.001 to 2 parts by mass, preferably 0.01 to 1 part by mass, relative to 100 parts by mass of a total amount of the polymerizable components.

A polymer having a unit derived from the compound in the first or the second aspect of the present invention has high oxygen permeability and excellent durability of mechanical strength in a buffered phosphate solution and dimension stability. Therefore, the present compounds are suitable as materials for preparing ophthalmic devices such as contact lenses, intraocular lenses and artificial corneas. A method for preparation of the ophthalmic device with the present polymer may be any conventional ones. For instance, a machining method and a molding method may be used for forming lenses such as contact lenses and intraocular lenses.

EXAMPLES

The present invention will be explained below in further detail with reference to a series of the Examples and the Comparative Examples, though the present invention is in no way limited by these Examples.

In the following descriptions, a viscosity was determined by a Cannon-Fenske viscosimeter and a specific gravity was as determined by a hydrometer. A refraction index was as determined by a digital refractometer RX-5000, ex Atago Co., Ltd. $^1$H-NMR analysis was conducted by JNM-ECP500, ex JEOL Ltd. with deuterochloroform as a measuring solvent. A ratio of a compound was determined by gas chromatography, i.e. GC. Conditions in GC were as follows.

[GC Conditions]
Gas chromatograph: ex Agilent Technologies, Inc.
Detector: FID, temperature of 300 degrees C.
Capillary Column: HP-5MS (0.25 mm×30 m×0.25 micrometer), ex J & W
Temperature rise program: 50 degrees C. for 5 minutes, 10 degrees C./minute and, then, maintained at 250 degrees C.
Temperature at an inlet: 250 degrees C.
Carrier gas: Helium with a flow rate of 1.0 ml/minute
Split ratio: 50:1
Injection volume: 1 microlitter Synthesis Example 1

In a one-liter flask equipped with a stirring device, a dimroth condenser, a thermometer and a dropping funnel, put were 76.5 g (0.75 mol) of ethylene glycol monoallyl ether and 100 g of toluene, and heated to 70 degrees C. 0.38 Gram of a solution of a catalyst, complex of alkali-neutralized chloroplatinic acid with vinyl siloxane, in toluene, containing 0.5% of platinum, was added in the flask. Then, 206 g (0.5 mol) of 1-butyl-9-hydro-1,1,3,3,5,5,7,7,9,9-decamethylpentasiloxane was added dropwise in the flask with the dropping funnel over one hour. The internal temperature rose up to 85 degrees C. The reaction mixture was held at 100 degrees C. for one hour and, then, analyzed in GC. The peak of the raw material, monobutyl decamethyl hydropentasiloxane, disappeared, which means that the reaction completed. 200 Gram of ion exchanged water was added to the reaction mixture with stirring to wash it and, then, left standing to cause a phase separation. The aqueous phase containing the excessive ethylene glycol monoallyl ether was removed. The organic phase was washed similarly twice with each 200 g of ion exchanged water and, then, the toluene in the organic phase was stripped off under a reduced pressure to obtain 242 g of a colorless and transparent liquid, silicone compound represented by the following formula (8). The yield was 94%. The ratio of the silicone compound represented by the following formula (8) in the obtained compound was 99.4 mass %, as determined in GC.

silicone compound fell down below the detection limit by GC and, then, 4.0 g (0.125 mol) of methanol was added to the reaction mixture. Further, 180 g of hexane and 180 g of ion exchanged water were added to the reaction mixture to wash it. The reaction mixture was left standing to cause a phase separation. The aqueous phase was removed and, subsequently, the organic phase was washed twice with ion exchanged water. The solvent, hexane, was stripped off from the organic phase under a reduced pressure to obtain 147 g of a colorless and transparent liquid product. $^1$H-NMR analysis showed that the obtained compound in the product was a silicone compound represented by the following formula (10), hereinafter referred to as silicone compound 1-1. The yield was 88% and the aforesaid amount was 0.22 mol. The ratio of the silicone compound represented by the following formula (10) in the product was 97.3 mass %, as determined in GC, the viscosity was 32.6 mm$^2$/s at 25 degrees C., the specific gravity was 0.993 at 25 degrees C. and the refraction index was 1.4381.

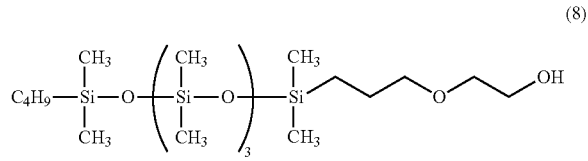

(8)

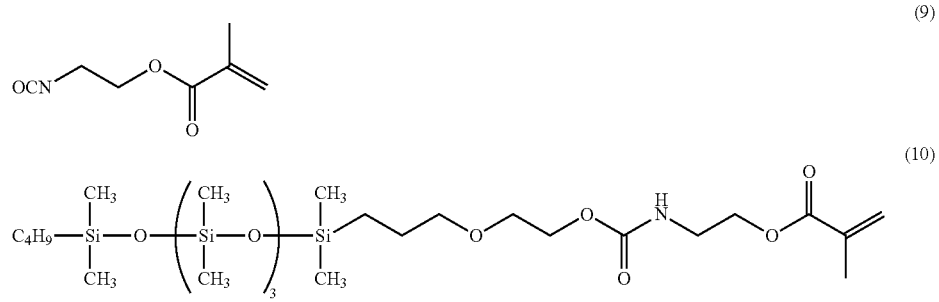

(9)

(10)

(1) Preparation of a Compound of the First Aspect of the Present Invention

Example 1-1

In a one-liter flask equipped with a stirring device, a dimroth condenser, a thermometer and a dropping funnel, put were 128.5 g (0.25 mol) of the silicone compound represented by the formula (8), 0.01 g (0.01 mass %) of dioctyl tin oxide, 0.01 g of Ionol, i.e. BHT, and 0.01 g of 4-methoxyphenol. 40.3 Gram (0.26 mol) of a methacryl group-containing isocyanate compound represented by the following formula (9) was added dropwise to the mixture over one hour. The internal temperature rose from 20 degrees C. up to 40 degrees C. The mixture was held at 40 degrees C., while monitoring the peak of the silicone compound represented by the formula (8) in GC. Four hours later, the intensity of the peak of the Example 1-2

The procedures of Example 1-1 were repeated, except that 30.9 g (0.26 mol) of a methacryl group-containing isocyanate compound represented by the following formula (11) was used in place of 40.3 g (0.26 mol) of a methacryl group-containing isocyanate compound represented by the formula (9). 128.3 Gram of a colorless and transparent liquid product was obtained. $^1$H-NMR analysis showed that the obtained compound in the product was a silicone compound represented by the following formula (12), hereinafter referred to as silicone compound 1-2. The yield was 90% and the aforesaid amount was 0.18 mol. The ratio of the silicone compound represented by the following formula (12) in the product was 96.5 mass %, as determined in GC, the viscosity was 29.5 mm$^2$/s at 25 degrees C., the specific gravity was 0.995 at 25 degrees C. and the refraction index was 1.4382.

(11)

-continued

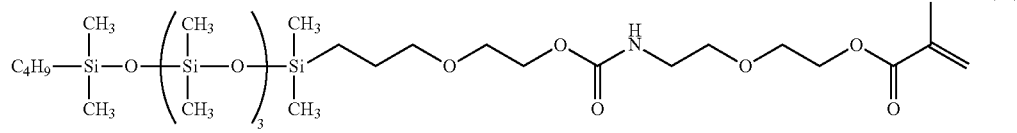

(12)

Synthesis Example 1-3

In a two-litter flask equipped with a stirring device, a dimroth condenser, a thermometer and a dropping funnel, put were 205.6 g (0.4 mol) of the silicone compound represented by the formula (8), 50.6 g (0.5 mol) of triethylamine as a de-hydrochloric acid agent, and 500 g of hexane. Then, a mixture of 48.1 g (0.46 mol) of methacrylic acid chloride and 50 g of hexane was added dropwise over one hour while cooling the flask in a water bath. The internal temperature rose from 20 degrees C. up to 30 degrees C. The water bath was removed and the reaction mixture was held at room temperature, while monitoring the peak of the silicone compound represented by the formula (8) in GC. Ten hours later, the intensity of the peak of the silicone compound fell down below the detection limit by GC and, then, 500 g of ion exchanged water was added to the reaction mixture to wash it. The reaction mixture was left standing to cause a phase separation. The aqueous phase was removed. The organic phase was washed twice with water. The solvent, hexane, was stripped off from the organic phase under a reduced pressure to obtain 206 g of a colorless and transparent liquid product. $^1$H-NMR analysis showed that the obtained compound in the product was a silicone compound represented by the following formula (13), hereinafter referred to as silicone compound 1-3. The yield was 89%. The ratio of the silicone compound represented by the following formula (13) in the product was 98.5 mass %, as determined in GC, the viscosity was 5.9 mm$^2$/s at 25 degrees C., the specific gravity was 0.944 at 25 degrees C. and the refraction index was 1.4260.

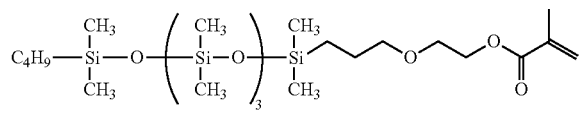

(13)

cause a phase separation. The aqueous phase was removed. The organic phase was washed twice with an aqueous 5% solution of sodium sulfate. Toluene in the organic phase was stripped off from the organic phase under a reduced pressure to obtain 240 g of a silicone compound represented by the following formula (14). The yield was 67%. The ratio of the silicone compound represented by the following formula (14) was 99.1 mass %, as determined in GC.

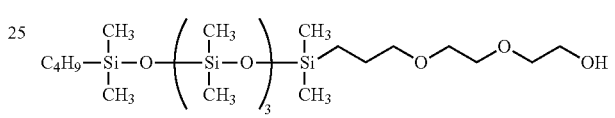

(14)

The procedures of Synthesis Example 1-3 were repeated, except that 223.2 g (0.4 mol) of the silicone compound represented by the formula (14) was used in place of 205.6 g of the silicone compound represented by the formula (8). 5% Aqueous solution of sodium sulfate was used in place of ion exchanged water to wash the resulting product. The solvent, hexane, was stripped off from the organic phase under a reduced pressure to obtain 213 g of a colorless and transparent liquid product. $^1$H-NMR analysis showed that the obtained compound in the product was a silicone compound represented by the following formula (15), hereinafter referred to as silicone compound 1-4. The yield was 85%. The ratio of the silicone compound represented by the following formula (15) in the product was 97.7 mass %, as determined in GC, the viscosity was 6.4 mm$^2$/s at 25 degrees C., the specific gravity was 0.945 at 25 degrees C. and the refraction index was 1.4267.

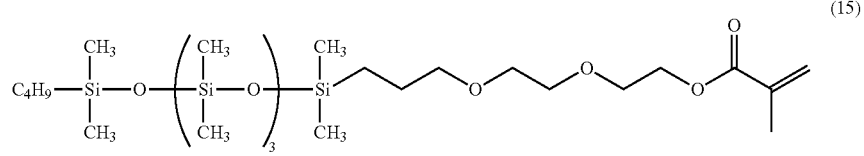

(15)

Synthesis Example 1-4

The procedures of Synthesis Example 1 were repeated, except that 109.5 g (0.75 mol) of diethylene glycol monoallyl ether was used in place of 76.5 g (0.75 mol) of ethylene glycol monoallyl ether. After the reaction was completed, the reaction product was washed with 200 g of aqueous 5% solution of sodium sulfate. The reaction mixture was left standing to

Synthesis Example 1-5

The procedures of Example 1-1 were repeated, except that 139.5 g (0.25 mol) of the silicone compound represented by the formula (14) prepared in Synthesis Example 1-4 was used in place of 143 g (0.25 mol) of the silicone compound represented by the formula (8). 164 Gram of a colorless and transparent liquid product was obtained. $^1$H-NMR analysis showed that the obtained compound in the product was a silicone compound represented by the following formula (16), hereinafter referred to as silicone compound 1-5. The yield was 92% and the aforesaid amount was 0.23 mol. The ratio of the silicone compound represented by the following formula (16) in the product was 96.3 mass %, as determined in GC, the viscosity was 34.5=²/s at 25 degrees C., the specific gravity was 0.990 at 25 degrees C. and the refraction index was 1.4373.

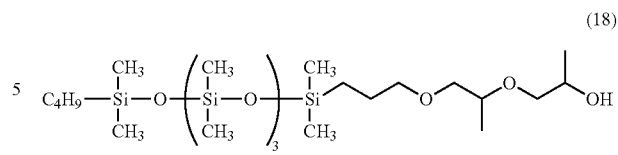

(18)

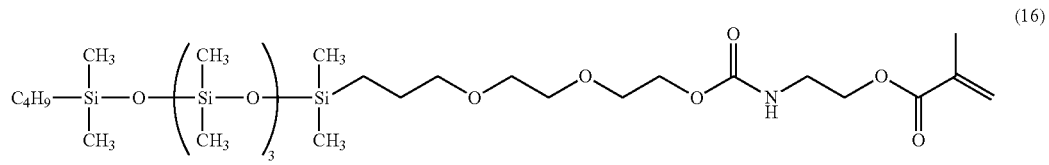

(16)

Synthesis Example 1-6

The procedures of Example 1-2 were repeated, except that 139.5 g (0.25 mol) of the silicone compound represented by the formula (14) prepared in Synthesis Example 1-4 was used in place of 143 g (0.25 mol) of the silicone compound represented by the formula (8). 174.1 Gram of a colorless and transparent liquid product was obtained. ¹H-NMR analysis showed that the obtained compound in the product was a silicone compound represented by the following formula (17), hereinafter referred to as silicone compound 1-6. The yield was 96.3% and the aforesaid amount was 0.23 mol. The ratio of the silicone compound represented by the following formula (17) in the product was 92 mass %, as determined in GC, the viscosity was 30.8 mm²/s at 25 degrees C., the specific gravity was 0.999 at 25 degrees C. and the refraction index was 1.4371.

The procedures of Example 1-2 were repeated, except that 146.5 g (0.25 mol) of the silicone compound represented by the formula (18) was used in place of 139.5 of the silicone compound represented by the formula (8). 163.0 Gram of a colorless and transparent liquid product was obtained. ¹H-NMR analysis showed that the obtained compound in the product was a silicone compound represented by the following formula (19), hereinafter referred to as silicone compound 1-7. The yield was 88% and the aforesaid amount was 0.22 mol. The ratio of the silicone compound represented by the following formula (19) in the product was 96.6 mass %, as determined in GC, the viscosity was 35.3 mm²/s at 25 degrees C., the specific gravity was 1.003 at 25 degrees C. and the refraction index was 1.4392.

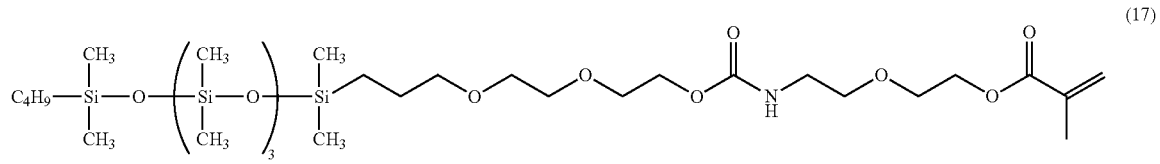

(17)

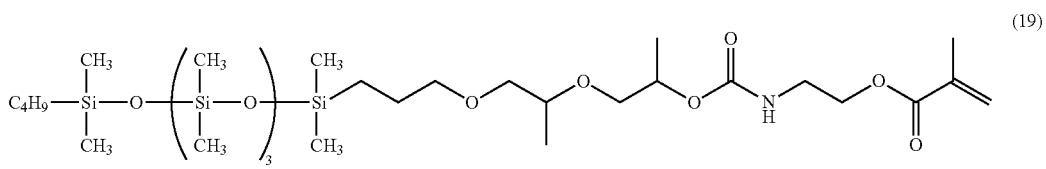

(19)

Synthesis Example 1-7

The procedures of Synthesis Example 1 were repeated, except that 130.5 g (0.75 mol) of dipropylene glycol monoallyl ether was used in place of 76.5 g (0.75 mol) of ethylene glycol monoallyl ether. 254.9 Gram (0.43 mol) of a colorless and transparent liquid silicone compound represented by the following formula (18) was obtained. The yield was 87%. The ratio of the silicone compound represented by the following formula (18) was 99.2 mass %, as determined in GC.

(2) Preparation of a Compound of the Second Aspect of the Present Invention

Example 2-1

In a one-liter flask equipped with a stirring device, a dimroth condenser, a thermometer and a dropping funnel, put were 128.5 g (0.25 mol) of the silicone compound represented by the formula (8), 0.01 g (0.01 mass %) of dioctyl tin oxide, 0.01 g of Ionol, i.e. BHT, and 0.01 g of 4-methoxyphenol. 62.1 Gram (0.26 mol) of an acryl group-containing isocyanate compound represented by the following formula (20) was added dropwise to the mixture over one hour. The internal temperature rose from 20 degrees C. up to 40 degrees C. The mixture was held at 90 degrees C., while monitoring the peak of the silicone compound represented by the formula (8) in GC. Four hours later, the intensity of the peak of the silicone compound, the formula (8), fell down below the detection limit by GC and, then, 4.0 g (0.125 mol) of methanol was added to the reaction mixture. Further, 180 g of hexane and 180 g of ion exchanged water were added to the reaction mixture to wash it. The reaction mixture was left standing to cause a phase separation. The aqueous phase was removed and, subsequently, the organic phase was washed twice with ion exchanged water. The solvent, hexane, was stripped off from the organic phase under a reduced pressure to obtain 150.6 g of a colorless and transparent liquid product. $^1$H-NMR analysis showed that the obtained compound in the product was a silicone compound represented by the following formula (21), hereinafter referred to as silicone compound 2-1. The yield was 80% and the aforesaid amount was 0.2 mol. The ratio of the silicone compound represented by the following formula (21) in the product was 97.5 mass %, as determined in GC, the viscosity was 90.0 mm$^2$/s at 25 degrees C., the specific gravity was 1.017 at 25 degrees C. and the refraction index was 1.4440. A chart of $^1$H-NMR spectra of the silicone compound 2-1 is shown in FIG. 1.

ration. The aqueous phase was removed. The organic phase was washed twice with water. The solvent, hexane, was stripped off from the organic phase under a reduced pressure to obtain 206 g of a colorless and transparent liquid product. $^1$H-NMR analysis showed that the obtained compound in the product was a silicone compound represented by the following formula (22), hereinafter referred to as silicone compound 2-2. The yield was 89%. The ratio of the silicone compound represented by the following formula (22) in the product was 98.5 mass %, as determined in GC, the viscosity was 5.9 mm$^2$/s at 25 degrees C., the specific gravity was 0.944 at 25 degrees C. and the refraction index was 1.4260.

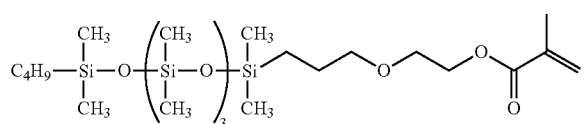
(22)

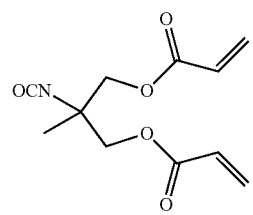
(20)

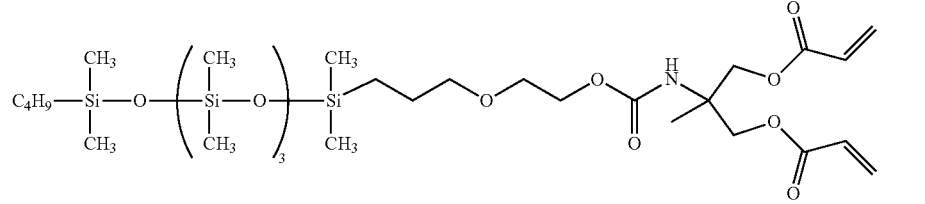
(21)

Synthesis Example 2-2

In a two-litter flask equipped with a stirring device, a dimroth condenser, a thermometer and a dropping funnel, put were 205.6 g (0.4 mol) of the silicone compound represented by the formula (8), 50.6 g (0.5 mol) of triethylamine as a dehydrochlorination agent, and 500 g of hexane. Then, a mixture of 48.1 g (0.46 mol) of methacrylic acid chloride and 50 g of hexane was added dropwise over one hour, while cooling the flask in a water bath. The internal temperature rose from 20 degrees C. up to 30 degrees C. The water bath was removed and the reaction mixture was held at room temperature, while monitoring the peak of the silicone compound represented by the formula (8) in GC. Ten hours later, the intensity of the peak of the silicone compound fell down below the detection limit by GC and, then, 500 g of ion exchanged water was added to the reaction mixture to wash it. The reaction mixture was left standing to cause a phase sepa- Synthesis Example 2-3

The procedures of Example 2-1 were repeated, except that 40.3 g (0.26 mol) of a methacryl group-containing isocyanate compound represented by the following formula (23) was used in place of 62.1 g (0.26 mol) of an acryl group-containing isocyanate compound represented by the formula (20). 147 Gram of a colorless and transparent liquid product was obtained. $^1$H-NMR analysis showed that the obtained compound in the product was a silicone compound represented by the following formula (24), hereinafter referred to as silicone compound 2-3. The yield was 88% and the aforesaid amount was 0.22 mol. The ratio of the silicone compound represented by the following formula (24) in the product was 97.3 mass % as determined in GC, the viscosity was 32.6 mm$^2$/s at 25 degrees C., the specific gravity was 0.993 at 25 degrees C. and the refraction index was 1.4381.

(23)

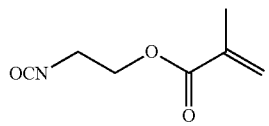

(24)

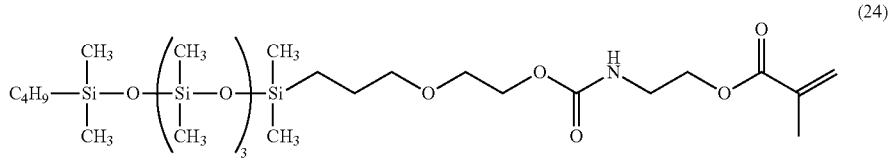

Synthesis Example 2-4

The silicone compound described in Example 1 in Patent Literature 7, Japanese Patent Application Laid-Open No. 2013-112776, was prepared.

In a one-litter flask equipped with a stirring device, a thermometer and a reflux condenser, put were 234.4 g of a polysiloxane which had a hydroxyl group at one terminal and is represented by the following formula:

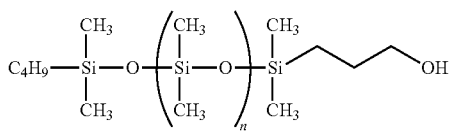

wherein n was 60 on average;
11.95 g of an isocyanate compound represented by the following formula, Karenz BEI, ex Showa Denko Co., Ltd.: OCN—C(CH$_3$) [CH$_2$—O—CO—CH=CH$_2$]$_2$;
246 g of toluene, and 0.25 g of dioctyl tin diacetate, and heated at 100 degrees C. for 8 hours. The peak of the isocyanate disappeared, as confirmed in IR and, then, the resulting mixture was subjected to stripping under a reduced pressure of 10 mmHg at 100 degrees C. to remove toluene to obtain a colorless and transparent liquid product. $^1$H-NMR analysis showed that the obtained compound in the product was the silicone compound represented by the following formula (25), hereinafter referred to as silicone compound 2-4. The silicone compound obtained was a mixture of compounds having various values of n with an average of 60 in the following formula. The viscosity was 87 mm$^2$/s at 25 degrees C., the volatile matter content was 0.4% after heated at 105 degrees C. for 3 hours, and the refraction index was 1.4082.

(25)

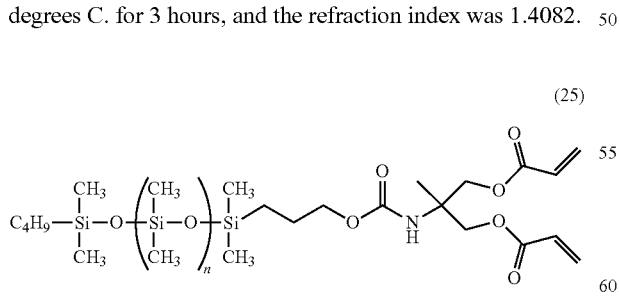

wherein n is 60 on average.

Synthesis Example 2-5

The procedures of Synthesis Example 1 were repeated, except that 43.5 g (0.75 mol) of allyl alcohol was used in place of 76.5 g (0.75 mol) of ethylene glycol monoallyl ether. 223 Gram of a colorless and transparent liquid product containing a silicone compound represented by the following formula (26) was obtained. The yield was 95%. The ratio of the silicone compound represented by the following formula (26) in the product was 99.6 mass %, as determined in GC.

(26)

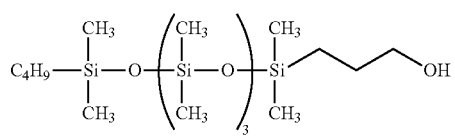

The procedures of Example 2-1 were repeated, except that 117.5 g (0.25 mol) of the silicone compound represented by the formula (26) was used in place of 128.5 g (0.25 mol) of the silicone compound represented by the formula (8). 145.3 Gram of a colorless and transparent liquid product was obtained. $^1$H-NMR analysis showed that the obtained compound in the product was a silicone compound represented by the following formula (27), hereinafter referred to as silicone compound 2-5. The yield was 82% and the aforesaid amount was 0.2 mol. The ratio of the silicone compound represented by the following formula (27) in the product was 97.8 mass %, as determined in GC, the viscosity was 75.6 mm$^2$/s at 25 degrees C., the specific gravity was 1.023 at 25 degrees C. and the refraction index was 1.4451.

(27)

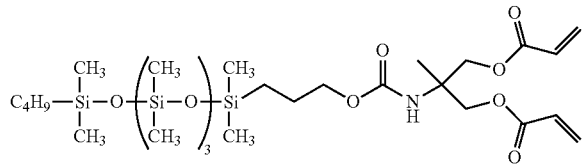

Synthesis Example 2-6

The procedures of Synthesis Example 1 were repeated, except that 142.5 g (0.75 mol) of triethylene glycol monoallyl ether was used in place of 76.5 g (0.75 mol) of ethylene glycol monoallyl ether. 273.9 Gram of a colorless and transparent liquid silicone compound represented by the following formula (28) was obtained. The yield was 91%. The ratio of the silicone compound represented by the following formula (28) was 99.1 mass %, as determined in GC.

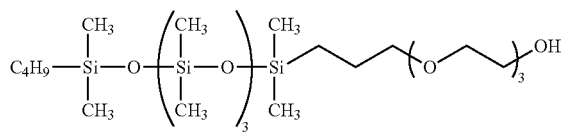
(28)

The procedures of Example 2-1 were repeated, except that 150.5 g (0.25 mol) of the silicone compound represented by the formula (28) was used in place of 128.5 g (0.25 mol) of the silicone compound represented by the formula (8). 168.2 Gram of a colorless and transparent liquid product was obtained. $^1$H-NMR analysis showed that the obtained compound in the product was a silicone compound represented by the following formula (29), hereinafter referred to as silicone compound 2-6. The yield was 80% and the aforesaid amount was 0.2 mol. The ratio of the silicone compound represented by the following formula (29) in the product was 97.8 mass %, as determined in GC, the viscosity was 96.2 mm$^2$/s at 25 degrees C., the specific gravity was 1.010 at 25 degrees C. and the refraction index was 1.437.

mold having two pieces of quartz glass plates which faced each other. The mixture was irradiated with light from an extra high pressure mercury lamp for one hour to obtain a film having a thickness of approximately 0.3 mm. The appearance of the film was observed visually.

3) Wettability, or Hydrophilicity, of a Film Surface, Composed of the Polymer

Water contact angles of the films prepared in 2) above were determined by a liquid drop method with a contact angle meter CA-D type, ex Kyowa Interface Science Co., LTD.

4) Stain Resistance of a Film, Composed of the Polymer

Two films for each one mixture were prepared in the same manner as in 2) above. One of the twos was soaked in a buffered phosphate solution, PBS(−), at 37 degrees C. for 24 hours. The film after soaked and another film without being soaked were stored in a well-known artificial lipid solution at 37 plus−minus 2 degrees C. for 8 hours. Then, the films were washed with PBS(−) and, subsequently, soaked in a 0.1% solution of sudan black sesame oil. When the colors were not different between the film after soaked and the film without being soaked, the film was evaluated as "good". When the color of the film after soaked was different between the film

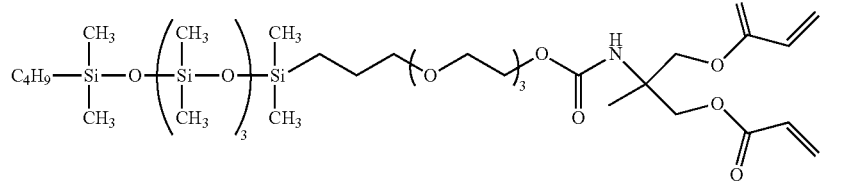
(29)

[Evaluations]

(1) Evaluation of the Compounds of the First Aspect of the Present Invention

The silicone compounds 1-1 to 1-7 prepared in Examples 1-1 and 1-2 and Synthesis Examples 1-3 to 1-7 were evaluated in the following manners. The results are as shown in Table 1.

1) Compatibility with Other Polymerizable Monomers

60 Parts by mass of one of the silicone compounds 1-1 to 1-7, 35 parts by mass of N, N-dimethyl acryl amide, 1 part by mass of triethylene glycol dimethacrylate, 5 parts by mass of trifluoroethyl methacrylate and 0.5 part by mass of darocur 1173, i.e., 2-hydroxy-2-methyl-1-phenyl-1-propanone, as a photopolymerization initiator, ex Ciba Specialty Chemicals Inc., were mixed and stirred. The appearances of the mixtures obtained were observed visually. A mixture comprising a silicone compound having good compatibility with the other compounds was colorless and transparent. In contrast, a mixture comprising a silicone compound having bad compatibility with the other compounds was turbid.

2) Appearance of a Film, Composed of the Polymer

The each mixture prepared in 1) above was deaerated in an argon atmosphere. The mixture obtained was poured into a without being soaked, that is, the film was stained with the sudan black sesame oil, the film was evaluated as "bad".

5) Durability of Mechanical Strength of a Film, Composed of the Polymer

Two films for each one mixture were prepared in the same manner as in 2) above. Any water on the surface of the films was wiped off. Then, one of the twos was soaked in a buffered phosphate solution, PBS(−), at 37 degrees C. for 24 hours. The film after soaked and another film without being soaked were cut into test samples having a dumbbell shape of a width of 2.0 mm. The top and the bottom of the test sample was held by a jig and pulled at a constant speed. Tensile strength and elongation at break were determined with a tensile tester AGS-50NJ, ex Shimadzu Corporation. When a change of the value of the tensile strength or the rupture elongation of the film after soaked, relative to the value of the film without being soaked was not larger than 10%, it was evaluated as "good". When a change of the value of the tensile strength or the rupture elongation of the film after soaked, relative to the value of the film without being soaked was larger than 10%, it was evaluated as "bad".

TABLE 1

|  | Example 1-1 | Example 1-2 | Comparative Example 1-1 | Comparative Example 1-2 | Comparative Example 1-3 | Comparative Example 1-4 | Comparative Example 1-5 |
|---|---|---|---|---|---|---|---|
| Silicone Compound | 1-1 | 1-2 | 1-3 | 1-4 | 1-5 | 1-6 | 1-7 |

TABLE 1-continued

|  | Example 1-1 | Example 1-2 | Comparative Example 1-1 | Comparative Example 1-2 | Comparative Example 1-3 | Comparative Example 1-4 | Comparative Example 1-5 |
|---|---|---|---|---|---|---|---|
| Compatibility | Colorless and transparent | Colorless and transparent | Slightly turbid | Turbid | Turbid | Turbid | Colorless and transparent |
| Appearance | Colorless and transparent | Colorless and transparent | Slightly turbid | Turbid | Turbid | Turbid | Colorless and transparent |
| Water contact angle, ° | 44 | 43 | 64 | 58 | 54 | 52 | 78 |
| Stain resistance | Good | Good | Bad | Bad | Bad | Bad | Good |
| Durability of a mechanical strength | Good | Good | Bad | Bad | Good | Good | Bad |

As shown in Table 1, the compound in the first aspect of the present invention was well compatible with the other (meth)acryl monomer and provided a colorless and transparent polymer. In particular, the present compound was well compatible with a fluorinated substituent group-containing methacryl compound, so that a polymer obtained had good hydrophilicity and stain resistance. Further, the present compound had a urethane bond and, therefore, the polymer obtained had excellent durability of mechanical strength.

In contrast, the compounds used in Comparative Examples 1-1 to 1-4 were less compatible with the other (meth)acryl monomers and did not provide a transparent polymer. Further, the polymer obtained in Comparative Example 5 where the monomer used had an oxypropylene-oxypropylene structure binding the urethane bond and the siloxane moiety had poor hydrophilicity.

(2) Evaluation of the Compounds of the Second Aspect of the Present Invention

The silicone compounds 2-1 to 2-6 prepared in Example 2-1 and Synthesis Examples 2-2 to 2-6 were evaluated in the following manners. In the following Comparative Example 2-6, triethylene glycol dimethacrylate was used in place of the silicone compounds 2-1 to 2-6. The results are as shown in Table 2.

In the following evaluation tests, a polymerizable silicone monomer, N, N-dimethyl acryl amide and trifluoroethyl methacrylate were used as the other polymerizable monomers. As the polymerizable silicone monomer, the silicone compound 2-2 prepared in Synthesis Example 2-2 was used.

1) Compatibility with Other Polymerizable Monomers

60 Parts by mass of the polymerizable silicone monomer, 35 parts by mass of N, N-dimethyl acryl amide, 5 parts by mass of trifluoroethyl methacrylate, 1 part by mass of one of the silicone compounds 2-2 to 2-6 or triethylene glycol dimethacrylate, as a cross-linkable agent, and 0.5 part by mass of darocur 1173, i.e., 2-hydroxy-2-methyl-1-phenyl-1-propanone, as a photopolymerization initiator, ex Ciba Specialty Chemicals Inc., were mixed and stirred.

The appearances of the mixtures obtained were observed visually. A mixture comprising a silicone compound having good compatibility with the other compounds was colorless and transparent. In contrast, a mixture comprising a silicone compound having bad compatibility with the other compounds was turbid.

2) Appearance of a Film, Composed of the Polymer

The each mixture prepared in (2), 1) above was deaerated in an argon atmosphere. The mixture obtained was poured into a mold having two pieces of quartz glass plates which faced each other. The mixture was irradiated with light from an extra high pressure mercury lamp for one hour to obtain a film having a thickness of approximately 0.3 mm. The appearance of the film was observed visually.

3) Wettability, or Hydrophilicity, of a Film Surface, Composed of the Polymer

Water contact angle of the film prepared in the test (2), 2) above was determined in the same manners as in (1), 3) above.

4) Stain Resistance of a Film, Composed of the Polymer

Two films for each one mixture were prepared in the same manner as in (2), 2) above. Stain Resistance of the film was evaluated in the same manners as in (1), 4) above.

5) Durability of Mechanical Strength of a Film, Polymer

Two films for each one mixture were prepared in the same manner as in (2), 2) above. Durability of mechanical strength of the film in a buffered phosphate solution was evaluated in the same manners as in (1), 5) above.

TABLE 2

|  | Example 2-1 | Comparative Example 2-1 | Comparative Example 2-2 | Comparative Example 2-3 | Comparative Example 2-4 | Comparative Example 2-5 | Comparative Example 2-6 |
|---|---|---|---|---|---|---|---|
| Polymerizable monomer | Silicone monomer: silicone compound 2-2, 60 parts by mass N,N,-dimethyl acryl amide, 35 parts by mass trifluoroethylmethacrylate, 5 parts by mass | | | | | | |
| Crosslinking component, 1 part by mass | Silicone compound 2-1 | Silicone compound 2-2 | Silicone compound 2-3 | Silicone compound 2-4 | Silicone compound 2-5 | Silicone compound 2-6 | Triethylene glycol dimethacrylate |
| Compatibility | Colorless and transparent | Slightly turbid | Slightly turbid | Turbid | Slightly turbid | Slightly turbid | Slightly turbid |
| Appearance | Colorless and transparent | Slightly turbid | Slightly turbid | Turbid | Slightly turbid | Slightly turbid | Slightly turbid |

TABLE 2-continued

| | Example 2-1 | Comparative Example 2-1 | Comparative Example 2-2 | Comparative Example 2-3 | Comparative Example 2-4 | Comparative Example 2-5 | Comparative Example 2-6 |
|---|---|---|---|---|---|---|---|
| Water contact angles, ° | 49 | 64 | 56 | 68 | 54 | 45 | 64 |
| Stain resistance | Good | Bad | Bad | Bad | Bad | Bad | Bad |
| Durability | Good | Bad | Good | Bad | Good | Bad | Bad |

As shown in Table 2, the compound in the second aspect of the present invention was well compatible with the other (meth)acryl monomers and provided a colorless and transparent polymer. In particular, the present compound was well compatible with a fluorinated substituent group-containing (meth)acryl monomer, so that provided a polymer having good stain resistance. Further, the polymer obtained had excellent durability of mechanical strength in a buffered phosphate solution and good hydrophilicity.

As shown in Table 2, Comparative Example 2-1, the compounds 2-2 prepared in Synthesis Example 2-2 was less compatible with the other (meth)acryl monomer compounds and did not provide a transparent mixture or polymer.

In contrast, as shown in Table 2, Example 2-1, when the present silicone compound was mixed with the mixture of silicone compound 2-2 and the other (meth)acryl compounds, a transparent mixture and polymer were provided. That is, the present silicone compound of the second aspect functioned well as a compatibilizing agent in addition to a crosslinking agent.

The silicone compound 2-3 had only one methacryl group. Therefore, as shown in Table 2, Comparative Example 2-2, the silicone compound 2-3 did not provide any transparent mixture or polymer. Further, the polymer obtained had poor stain resistance and hydrophilicity.

The silicone compound 2-4 had various values of n in the aforesaid formula, a longer silicone chain and a low hydrophilicity. Therefore, the silicone compound was less compatible with the other (meth)acryl compounds. The mixture obtained was turbid, so that the polymer obtained was not transparent. Further, the polymer obtained had poor durability of mechanical strength in a buffered phosphate solution, poor stain resistance and hydrophilicity.

The silicone compound 2-5 did not have oxyethylene structure in the spacer part. The silicone compound had a low hydrophilicity and was less compatible with the other (meth)acryl monomers. As shown in Table 2, Comparative Example 2-4, the compound did not provide a transparent polymer. Further, the polymer obtained had poor stain resistance and hydrophilicity.

The silicone compound 2-6 had two or more oxyethylenes at the spacer part. The silicone compound had too high hydrophilicity, so that the compound was less compatible with the other silicone monomer. As shown in Table 2, Comparative Example 2-5, the silicone compound did not provide a transparent polymer. Further, the silicone compound 2-6 had too long polyether spacer chain and, therefore, the polymer obtained had poor durability of mechanical strength in a buffered phosphate solution and poor stain resistance.

Triethylene glycol dimethacrylate does not have any silicone chain and has poor compatibility with a silicone monomer. Therefore, as shown in Table 2, Comparative Example 2-6, a transparent polymer was not provided.

INDUSTRIAL APPLICABILITY

The compound of the first aspect of the present invention copolymerized with polymerizable monomers to provide a colorless and transparent polymer having good oxygen permeability and good durability of mechanical strength in a buffered phosphate solution, in particular a polymer having good hydrophilicity and stain resistance.

The compound of the second aspect of the present invention is well compatible with the other polymerizable monomers, in particular (meth)acryl silicone monomers and fluorinated substituent group-containing (meth)acryl silicone monomers. A polymer having a unit derived from the present compound has good oxygen permeability, has colorlessness and transparency, and good durability of mechanical strength in a buffered phosphate solution, and, further has good hydrophilicity and stain resistance.

Further, the present method provides a compound having one specific structure at a high ratio and, therefore, provides a polymer having higher transparency. Accordingly, the present compound and the present method are useful for preparing ophthalmic devices such as contact lenses, intraocular lenses and artificial corneas.

The invention claimed is:

1. A compound represented by the following formula (1-1):

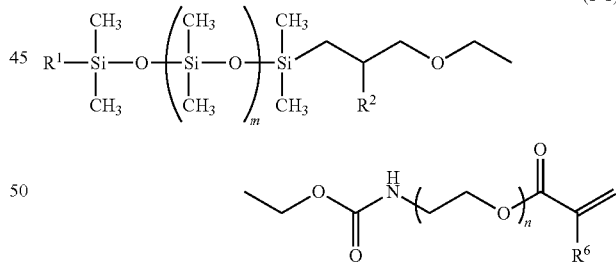

(1-1)

wherein m is 3, n is 1 or 2, $R^1$ is an alkyl group having 1 to 4 carbon atoms, and $R^2$ and $R^6$ are, independently of each other, a hydrogen atom or a methyl group, and wherein an amount of one kind of compound having each one value of m, n, $R^1$, $R^2$ and $R^6$ in the formula (1-1) is more than 95 mass % of a total mass of the compound.

2. A polymer comprising repeating units derived from the compound according to claim 1 and repeating units derived from at least one other compound having a group which is polymerizable with said compound.

3. An ophthalmic device composed of the polymer according to claim 2.

4. A compound represented by the following formula (2-1):

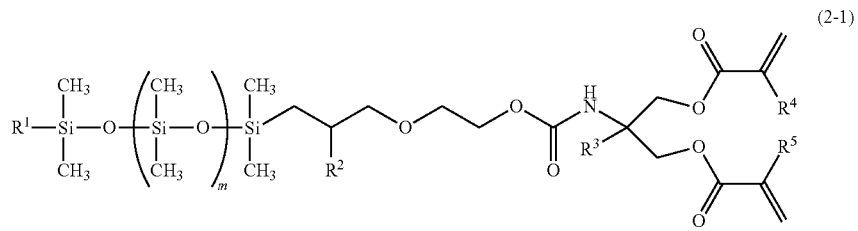

wherein m is an integer of from 2 to 10, $R^1$ is an alkyl group having 1 to 4 carbon atoms, $R^2$ is a hydrogen atom or a methyl group, $R^3$ is a substituted or unsubstituted monovalent hydrocarbon group which has no (meth) acryl group and has 1 to 20 carbon atoms, or an alkoxy group having 1 to 10 carbon atoms, $R^4$ is a hydrogen atom or a methyl group, and $R^5$ is a hydrogen atom or a methyl group.

5. The compound according to claim 4, wherein an amount of one kind of compound having each one value of m, $R^1$, $R^2$, $R^3$, $R^4$ and $R^5$ in the formula (2-1) is more than 95 mass % of a total mass of the compound.

6. The compound according to claim 4 or 5, wherein m in the formula (2-1) is 3.

7. A polymer comprising repeating units derived from the compound according to claim 4 and repeating units derived from at least one other compound having a group which is polymerizable with said compound.

8. The polymer according to claim 7, wherein the other compound includes a silicone monomer.

9. The polymer according to claim 8, wherein an amount of the compound of formula (2-1) is 0.1 to 50 parts by mass, relative to 100 parts by mass of the silicone monomer.

10. A method for preparing a compound represented by the following formula (1-1):

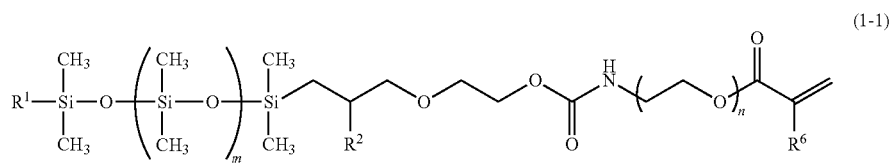

wherein m is 3, n is 1 or 2, $R^1$ is an alkyl group having 1 to 4 carbon atoms, and $R^2$ and $R^6$ are, independently of each other, a hydrogen atom or a methyl group, comprising a step of reacting a silicone compound represented by the following formula (3):

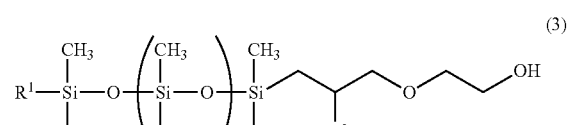

wherein m, $R^1$ and $R^2$ are as defined above;

with a (meth)acryl group-containing isocyanate compound represented by the following formula (4):

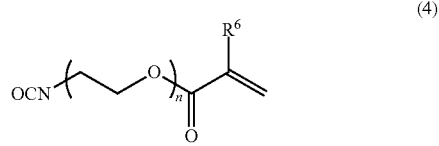

wherein n and $R^6$ are as defined above; and wherein an amount of one kind of compound having each one value of m, n, $R^1$, $R^2$ and $R^6$ in the formula (1-1) is more than 95 mass % of a total mass of the compound.

11. A method for preparing a compound represented by the following formula (2-1):

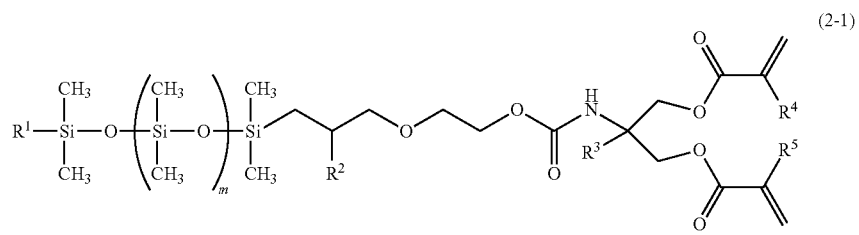

wherein m is an integer of from 2 to 10, $R^1$ is an alkyl group having 1 to 4 carbon atoms, $R^2$ is a hydrogen atom or a methyl group, $R^3$ is a substituted or unsubstituted monovalent hydrocarbon group, which has no any (meth)acryl group, having 1 to 20 carbon atoms or an alkoxy group having 1 to 10 carbon atoms, $R^4$ is a hydrogen atom or a methyl group, and $R^5$ is a hydrogen atom or a methyl group, comprising a step of reacting a silicone compound represented by the following formula (3):

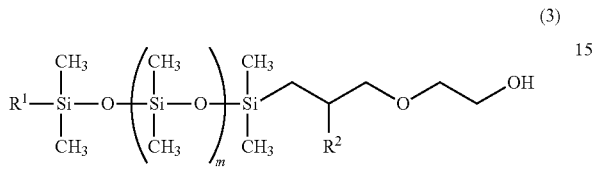

(3)

wherein m, $R^1$ and $R^2$ are as defined above;

with a (meth)acryl group-containing isocyanate compound represented by the following formula (5):

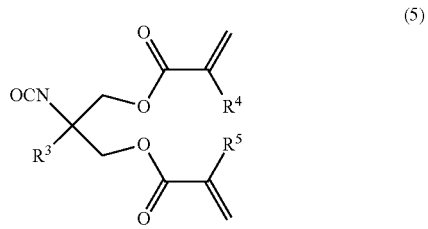

(5)

wherein $R^3$, $R^4$ and $R^5$ are as defined above.

12. The method according to claim 1, wherein an amount of one kind of compound having each one value of m, $R^1$, $R^2$, $R^3$, $R^4$ and $R^5$ in the formula (2-1) is more than 95 mass % of a total mass of the compound.

13. The method according to claim 12, wherein m in the formula (2-1) is 3.

* * * * *